US006733438B1

(12) United States Patent
Dann et al.

(10) Patent No.: US 6,733,438 B1
(45) Date of Patent: May 11, 2004

(54) FEMALE STIMULATION DEVICE

(76) Inventors: Jeffrey Dann, 44 Terrace Dr., Worcester, MA (US) 01609; David Gloth, 16 Harcourt St., Apt. 61, Boston, MA (US) 02116

( * ) Notice: Subject to any disclaimer, the term of this patent is extended or adjusted under 35 U.S.C. 154(b) by 0 days.

(21) Appl. No.: 10/328,698

(22) Filed: Dec. 23, 2002

(51) Int. Cl.[7] .................... A61F 5/00
(52) U.S. Cl. .................... 600/38
(58) Field of Search .................... 600/38–41, 29; 601/84

(56) References Cited

U.S. PATENT DOCUMENTS 4,033,338 A 7/1977 Igwebike
4,790,296 A 12/1988 Segal
5,693,002 A 12/1997 Tucker et al.
5,725,473 A 3/1998 Taylor
5,755,236 A 5/1998 Dann et al.
5,813,973 A * 9/1998 Gloth .................... 600/29
5,895,349 A * 4/1999 Tihon .................... 600/29
5,908,379 A 6/1999 Schaefer et al.
5,989,180 A * 11/1999 Norton .................... 600/29
6,099,463 A 8/2000 Hockhalter

FOREIGN PATENT DOCUMENTS

WO WO0028939 5/2000

* cited by examiner

*Primary Examiner*—Samuel G. Gilbert

(57) ABSTRACT

A female stimulation device comprising a resilient device body having a partially deformable tip portion, a flange and an intermediate side wall portion extending outwardly from the tip portion to the flange. In use, the tip portion is compressed to force air out of the device body and the flange is placed in contact with vaginal wall tissue so that the clitoris is encompassed by the device body. Release and restorative deformation of the tip portion causes a partial vacuum within the device body, which maintains the device in place and provides suction to the clitoris. The intermediate side wall portion is substantially non-deformable in response to deformation of the tip portion, as may be achieved with outwardly convex side walls, thereby preventing deleterious entrapment and compression of the clitoris. Pharmacologically active materials, such as vasoactive agents, substances, and medications, may be applied to the device for contact with the clitoris during use in order to further enhance female sexual function.

21 Claims, 9 Drawing Sheets

FEMALE STIMULATION DEVICE

CROSS-REFERENCE TO RELATED APPLICATIONS

Not Applicable.

STATEMENT REGARDING FEDERALLY SPONSORED RESEARCH

Not Applicable.

FIELD OF THE INVENTION

This invention relates generally to a device for increasing female sexual stimulation and, more specifically, to a device which provides suction on the female clitoris, thereby causing vascular engorgement and enhancing sexual satisfaction.

BACKGROUND OF THE INVENTION

Clitoral vascular engorgement plays an important role in female sexual arousal and overall sexual satisfaction. Sexual arousal results in smooth muscle relaxation and arterial vasodilation within the clitoris. The resultant increase in blood flow leads to tumescence of the glans clitoris and increased sexual arousal. A variety of diseases, such as arteriosclerosis and diabetes, may cause clitoral erectile insufficiency and reduced clitoral arterial flow. This, in turn, may lead to difficulty or inability to achieve clitoral tumescence, especially in women who suffer from Female Sexual Arousal Disorder (FSAD). FSAD may be expressed as a lack of either subjective excitement, genital lubrication or orgasmic function.

A variety of devices have been developed for stimulating female sexual response. The most common devices are vibrators and mechanical dildos which create friction against the clitoris. A more effective method of increasing clitoral engorgement, especially in women suffering from FSAD, is through use of suction. A partial vacuum placed over the clitoris creates negative pressure in the organ that is lower than the systolic blood pressure. This, in turn, promotes clitoral arterial inflow, resulting in increased vascular engorgement and sexual arousal. This effect is particularly pronounced in women with FSAD.

U.S. Pat. No. 5,725,473 issued to Taylor describes suction cups placed on the nipples and the upper portion of the vulva of the user. The suction cups are connected to a remotely located vacuum bulb through an elaborate array of tubes. Compression of the externally located bulb introduces a vacuum in the suction cups. The device, however, may be cumbersome to wear and does not appear to provide a focused vacuum to the clitoris.

U.S. Pat. No. 5,693,002 issued to Tucker describes a penile ring with an attached suction cup and vibratory motor. During coitus, the suction cup presses against the vaginal area of the wearer's partner. Given the rough motion of coitus, any suction achieved with the device is likely to be unfocused, brief and intermittent.

U.S. Pat. No. 6,099,463 issued to Hockhalter describes a tubular suction chamber sized to fit over the clitoris and connected through tubing to an externally located, variable partial vacuum source such as the mouth of the user, a vacuum bulb or a mechanical pump. The force of the suction may be controlled by a check valve which is also used to release the partial vacuum. International Publication No. WO/28939 by Hovland describes a similar device to Hockhalter, utilizing a clitoral suction applicator connected to an externally located, hand-held, electronic pump. Both of these devices require the use of an external vacuum source connected via tubing to the suction chamber. The multi-component aspect of these devices makes them cumbersome to use, requiring the user to hold the device in place while the vacuum is applied.

U.S. Pat. Nos. 5,755,236 and 5,908,379 issued to Dann, et al. and to Schaefer, et al., respectively, both describe a vacuum producing, partially deformable device of unitary construction having a distal tip portion, a flange and intermediate frustoconical side walls which, when placed over the urinary meatus of the user, prevents urinary incontinence. Upon compression and release, the device described by Schaefer et al. causes collapse of the intermediate frustoconical side walls and drawing of the urinary meatus into the narrower tip portion. The meatus is compressed within the tip portion, thereby preventing urinary leakage from stress urinary incontinence. In practice, however, the device can cause pinching of urinary meatal tissue with discomfort and potential tissue injury. In the device described by Dann et al., the length of the intermediate frustoconical side walls is selected so as to increase the effective distance from the tip portion to the meatus, thereby minimizing entrapment of tissue in the tip portion and relying on gentler compression by the intermediate side walls. Both of these devices rely on inward deformation of the intermediate side walls in order to create urinary meatal compression and obstruction and to thereby prevent stress urinary incontinence.

SUMMARY OF THE INVENTION

In accordance with the invention, a device for stimulating the clitoris of a female includes a resilient and at least partially deformable device body having an enclosed tip portion, a flange, and an intermediate side wall portion extending outwardly from the tip portion to the flange. The device body is sized to encompass the clitoris of the user and, in one illustrative embodiment, the device body is of unitary construction. In use, the device body is placed over the clitoris of the user and the tip portion is deformed, causing a vacuum environment to be formed in an interior chamber formed by the device body. The vacuum environment maintains the device in reliable sealed engagement around the clitoris.

With this arrangement, a small, simple, and effective female clitoral stimulation device provides suction to the clitoris thereby stimulating vascular engorgement and sexual arousal. Advantageously, the device does not require an external vacuum source or associated tubing or connections and is simple to use, permitting the user to perform her daily activities while wearing it in an undetectable and discreet fashion.

The intermediate side wall portion is substantially non-deformable in response to deformation of the tip portion. One such illustrative side wall portion has an outwardly convex shape. With this arrangement, a substantially fixed volume lower vacuum chamber is formed over the clitoris so as to prevent side wall abutment and associated tissue compression or injury. To further reinforce the structure of the lower vacuum chamber so as to resist deformation, internal and/or external protuberances may be provided on the outwardly convex intermediate side walls.

A bio-compatible lubricant or adhesive may be applied to the flange in order to enhance the vacuum seal. The labia of the vagina cover the device, further securing it in place and permitting it to be worn in a discreet fashion during daily activities.

The device may be provided with a pharmacologically active material, such as vasoactive agents, substances, medications or herbs, which, in use, comes into continuous contact with the clitoris of the user, so as to further increase clitoral blood flow and sexual arousal. In one embodiment, the pharmacologically active material is disposed on the flange. In another embodiment, the pharmacologically active material is disposed within the device body and is released to contact the clitoris in response to deformation of the tip portion. In yet another embodiment, the pharmacologically active material is embedded in a wall of the device. Also described are various shapes for features of the device, which shapes vary the precision of the anatomical fit over the clitoris.

A method for increasing female sexual stimulation includes placing on the clitoris of the user a device body having a tip portion, a flange, and an intermediate side wall portion extending outwardly from the tip portion to the flange so that the device body encompasses the clitoris. The method further includes deforming the tip portion so as to create a vacuum chamber within the device body. Preferably, the intermediate side wall portion is substantially non-deformable in response to deformation of the tip portion. In one embodiment, this advantage is achieved by providing the intermediate wall portions with an outwardly convex shape. With this arrangement, a vacuum chamber is formed over the clitoris of the user in a simple manner that prevents pinching or compression of the clitoris.

According to a further aspect of the invention, a drug delivery method includes providing the device body with a pharmacologically active material to contact the clitoris of the user in use. In one embodiment, the pharmacologically active material is provided in the device body so as to contact the clitoris of the user in response to deformation of the tip portion and, in another embodiment, the pharmacologically active material is provided on the flange so as to contact the clitoris of the user in use. In yet another embodiment, the pharmacologically active material is embedded in a wall of the device and is released upon contact with the vaginal mucosa. Examples of suitable pharmacologically active materials include vasoactive agents, substances, medications or herbs.

BRIEF DESCRIPTION OF THE DRAWINGS

The foregoing features of this invention, as well as the invention itself, may be fully understood from the following detailed description of the drawings in which.

DETAILED DESCRIPTION OF THE INVENTION

Figure 1:
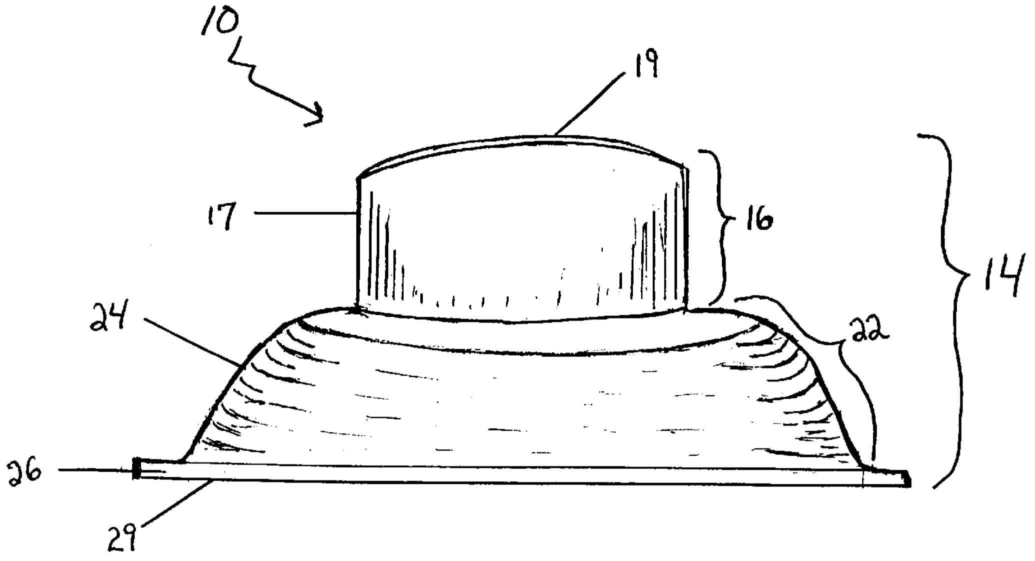
FIG. 1 is a side view of a female stimulation device in accordance with the invention.
Figure 1A:
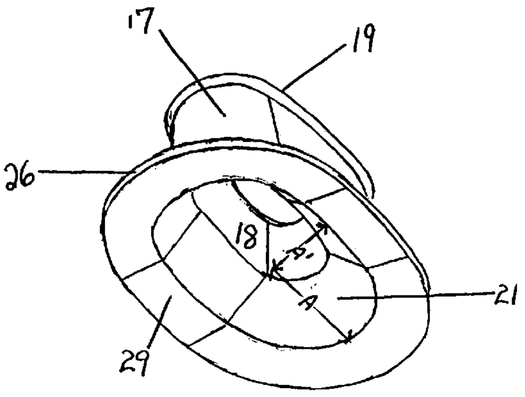
FIG. 1A is a bottom perspective view of the device of FIG. 1.
Figure 1B:
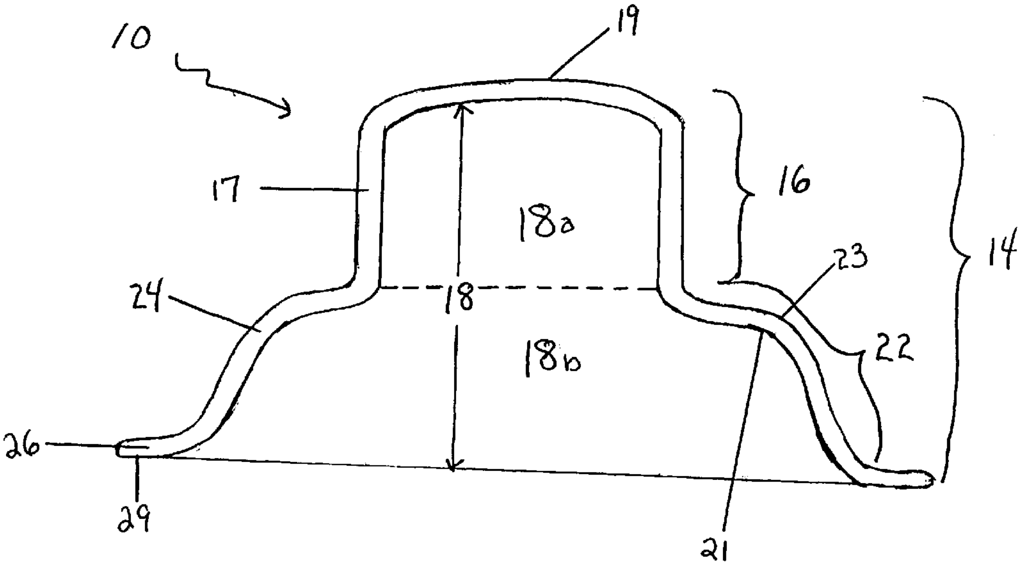
FIG. 1B is a cross-sectional side view of the device of FIG. 1.

Referring to FIGS. 1, 1A and 1B, a female stimulation device 10 includes a device body 14 having a tip portion 16 distal from the user's body, a flange 26 and a substantially non-deformable intermediate side wall portion 22 extending outwardly from the tip portion to the flange. The device body 14 defines an interior vacuum chamber 18 extending from the curved outer end wall 19 of the tip portion 16 to the flange 26. The interior vacuum chamber 18 is comprised of two sub-chambers; a deformable vacuum producing upper chamber **18*a* and a non-deformable vacuum reservoir lower chamber 18*b*, which chambers are exposed to one another in use, as will become apparent. The flange 26 includes a body-contacting surface 29**.

The tip portion 16 has a substantially oval shape with vertical walls 17 and a curved outer end wall 19 which serves as a gripping portion to facilitate application and removal of the device in the manner described below. In an alternate embodiment, the outer end wall 19 of the tip portion 16 is flat. The interior of the tip portion 16 defines the upper vacuum chamber **18*a*. The tip portion 16 is at least partially deformable, or compressible in order to produce a partial vacuum within the interior vacuum chamber 18 sufficient to seal the device 10 to the user's body by the differential in air pressure between the air within the vacuum chamber 18** and the atmospheric air pressure.

The intermediate side wall portion 22 extends outwardly from the bottom of the tip portion 16 to the flange 26. The interior of the intermediate side wall portion 22 forms the lower vacuum chamber **18*b***.

The intermediate side wall portion 22 is designed so as to avoid compression of the clitoris. In the illustrative embodiment, the intermediate side wall portion is substantially non-deformable and maintains its shape when vacuum is applied by compression of the tip portion. Thus, the volume of the lower vacuum chamber **18*b* is substantially constant. In a preferred embodiment, the intermediate side wall portion 22 is outwardly convex. With this arrangement, the intermediate side walls' 24 are prevented from folding inward and abutting when vacuum is applied. This, in turn, prevents pinching or compression of the clitoris which is positioned within the lower vacuum chamber 18***b* (FIG. 6A).

Figure 2:
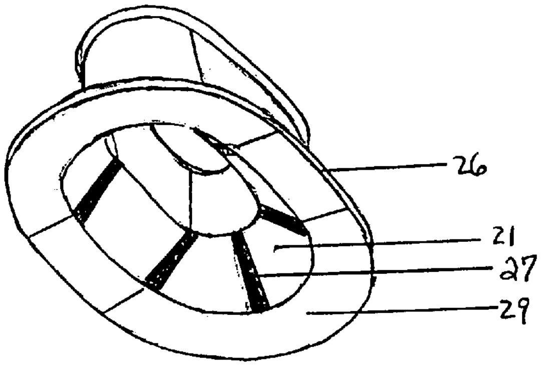
FIG. 2 is a bottom perspective view of a female stimulation device according to an alternate embodiment of the invention in which reinforcing protuberances are provided on an inner surface of the intermediate side wall portion.
Figure 2A:
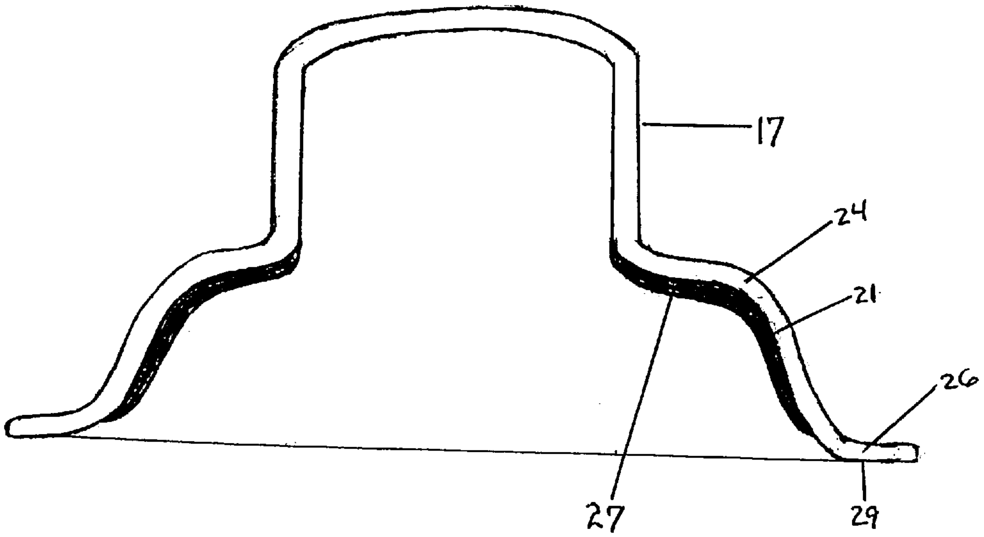
FIG. 2A is a cross-sectional side view of the device of FIG. 2.

In a further embodiment shown in FIGS. 2 and 2A, in which like reference numbers refer to like elements, the non-deformable aspect of the intermediate side wall portion 22 is reinforced by a plurality of protuberances 27 which extend along at least a portion of the inner surface 21 of the intermediate side walls 24. The protuberances 27 function as reinforcing arches to enhance the resistance of the intermediate side wall portion 22 to deformation in response to deformation of the tip portion.

Figure 3:
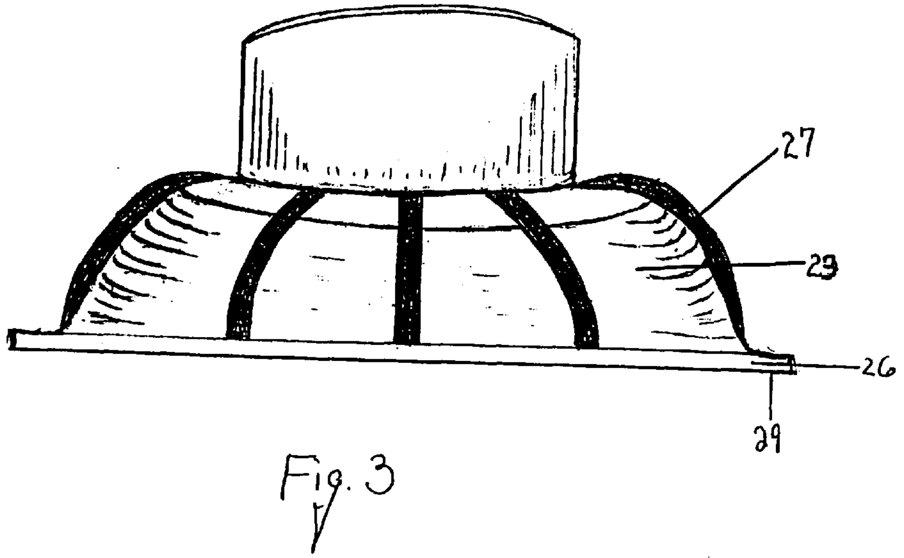
FIG. 3 is a side view of a female stimulation device according to a further embodiment of the invention in which reinforcing protuberances are provided on an outer surface of the intermediate side wall portion.
Figure 3A:
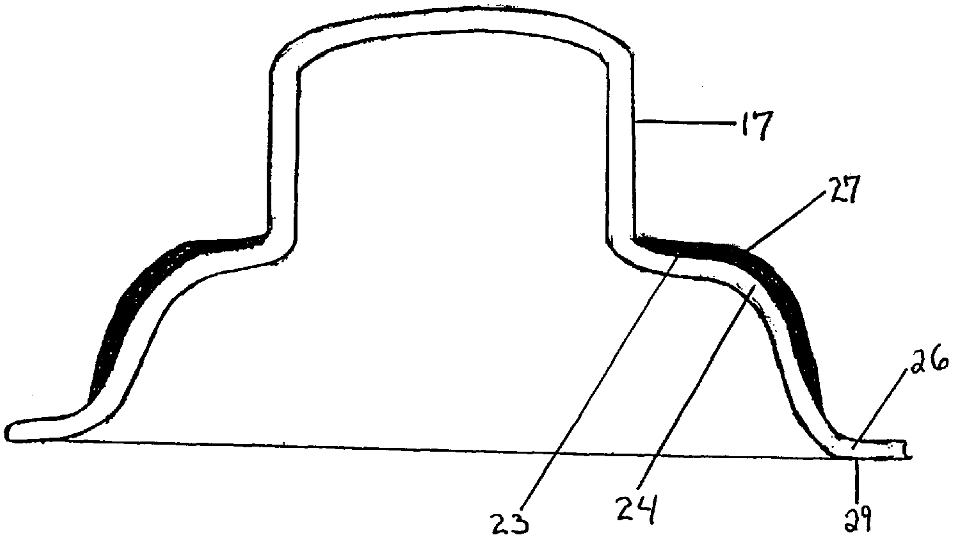
FIG. 3A is a cross-sectional side view of the device of FIG. 3.

Referring to the further embodiment of FIGS. 3 and 3A, in which like reference numbers refer to like elements, a plurality of reinforcing protuberances 27 extend along the outer surface 23 of the intermediate side walls 24. Preferably, in the embodiments of FIGS. 2 and 3, there are approximately 4 to 8 protuberances, although it will be appreciated that the number, size, shape, and location of the protuberances may vary. For example, protuberances may be provided both along the outer surface 23 and along the inner surface 21 of the intermediate side walls 24. As described above, maintenance of the outwardly convex geometry of the intermediate side walls 24 prevents inward folding, abutment and tissue compression and entrapment.

The body-contacting surface 29 of the flange 26 forms a continuous seal around the clitoris of the user. The seal may be enhanced with the use of an adhesive material or non-adhesive lubricant, such as water-based gels, petroleum-based gels, or hydrophilic, water-soluble polymers disposed on the body-contacting surface 29 of the flange 26.

Typically, the device 10 is of unitary construction. Alternatively, however, portions of the device may be separately constructed and joined thereafter. The device 10 is constructed of any resilient and at least partially deformable material suitable for application to the human body in the manner described. In the preferred embodiment, the device is comprised of silicone, thermoplastic elastomer, urethane or rubber material. It will be appreciated that although the intermediate side walls 24 are comprised of a deformable material, the side walls are made substantially non-deformable in response to deformation of the tip portion by their geometry (e.g., outwardly convex) and optionally also by the use of reinforcing protuberances 27 (FIGS. 2 and 3). As will be further appreciated, other manners of rendering the side walls 24 substantially non-deformable in response to deformation of the tip portion are possible, including, but not limited to one or more of material selection, geometry, dimensions, and reinforcing features.

In general, the device dimensions are dictated by the typical female anatomy so as to comfortably fit over the clitoris within the anterior vaginal vestibule. In the preferred embodiment, the outer radii A and A' (FIG. 1A) extending from the center of the device to the ends of the intermediate side wall portion 22 may vary between 0.50 cm and 1.75 cm depending upon the size and acuity of the oval shape. The radii of the tip portion 16 will vary in proportion to the dimensions stated above, but generally will be between 0.25 cm and 0.75 cm, respectively. Preferably, the body-contacting surface of the flange 26 contacts vaginal tissue adjacent to the outer perimeter of the clitoris. With this arrangement, the efficacy of the device is enhanced by providing a focused vacuum area. The height of the device 10 can also vary but should comfortably fit within the anterior vaginal vestibule without excessive protrusion. In the preferred embodiment, the height is on the order of approximately 2 cm. It will be appreciated however, that the exact dimensions of the device 10 can vary without departing from the spirit of the invention.

The shape of the device 10 can also vary without departing from the spirit of the invention. In the embodiment of FIGS. 1–1B, the device portions, including the tip portion 16, the convex intermediate side wall portion 22 and the flange 26, have a substantially oval or ellipsoid shape. The device 10 is positioned over the clitoris of the user within the anterior vaginal vestibule so that its long axis is parallel to the anterior-posterior axis of the vaginal vault. In this orientation, the erogenous tissue of the clitoris is adequately covered while the vertical length of the labial folds secure the device in place.

Figure 4:
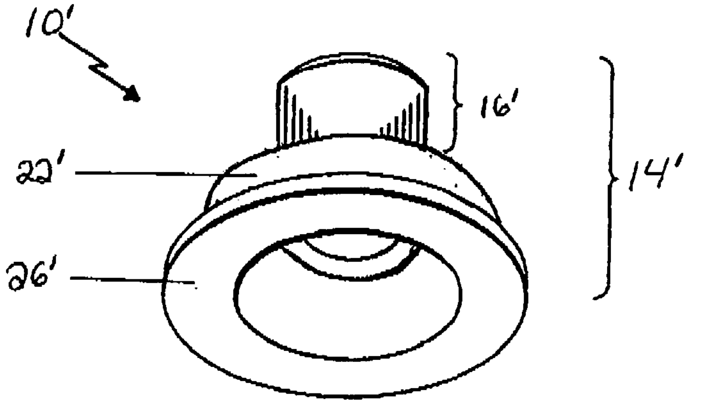
FIG. 4 is a bottom perspective view of a female stimulation device according to a further embodiment of the invention.
Figure 4A:
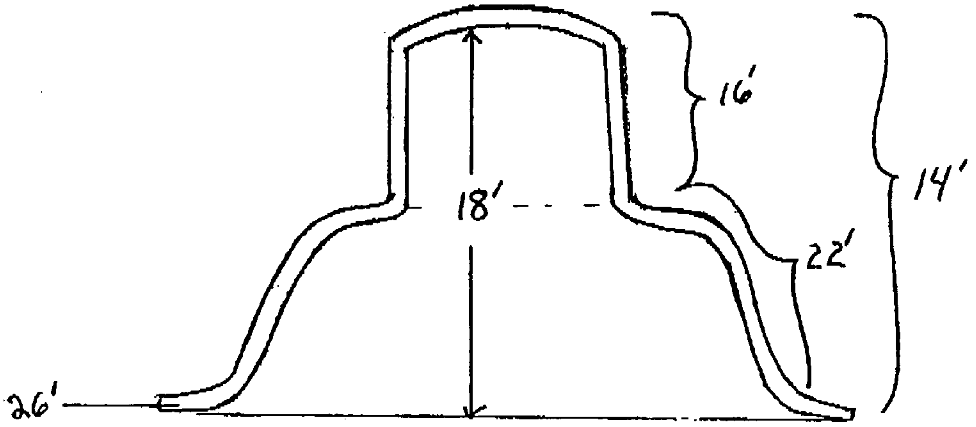
FIG. 4A is a cross-sectional side view of the device of FIG. 4.

Referring to FIGS. 4 and 4A, another embodiment of the device 10' is described, in which like elements have like reference numbers, but with the reference numbers of the device 10' having a prime symbol to indicate that they differ from like elements of FIG. 1 in shape, but not in function. Thus device 10' includes a device body 14' having a tip portion 16', a flange 26', and a substantially non-deformable intermediate side wall portion 22' configured as shown. The device 10' differs from device 10 (FIG. 1) in that the elements of device 10' have a substantially circular shape, as shown. The device 10' is positioned over the clitoris of the user so that the clitoris is substantially centered within the flange 26'.

Figure 5:
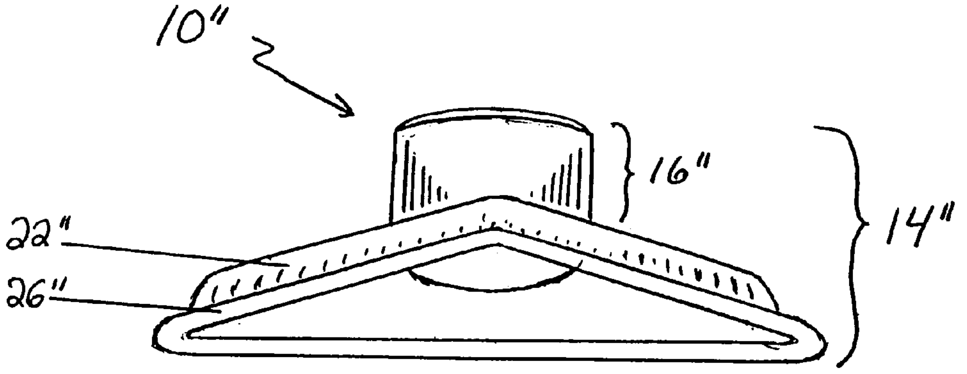
FIG. 5 is a perspective view of a female stimulation device according to a further embodiment of the invention.

Another embodiment of the device 10' is shown in FIG. 5 to have like elements, but a further alternative shape. The device 10" includes a device body 14" having a tip portion 16", a flange 26", and a substantially non-deformable side wall portion 22". In this embodiment, the flange 26" and sidewall portion 22" are substantially triangular in shape and the tip portion 16" is substantially circular or oval in shape. This embodiment provides the advantage of a close anatomical fit within the crus of the labial folds as they join anteriorly.

Figure 6:
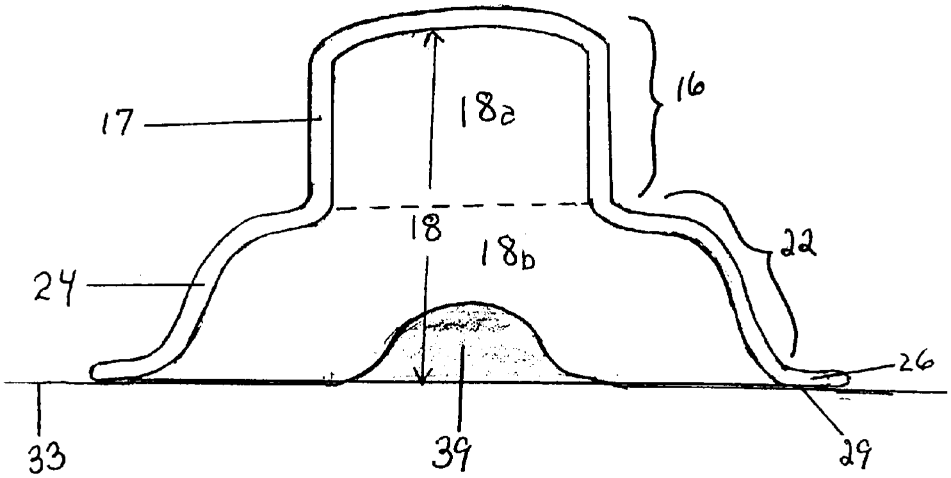
FIG. 6 is a cross-sectional side view of the device of FIG. 1 positioned over the clitoris of the user, but not in use since no vacuum environment exists.
Figure 6A:
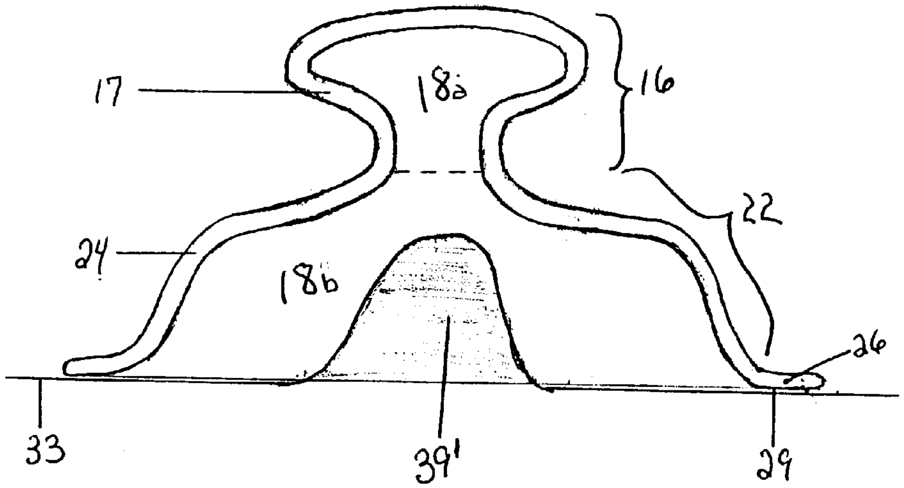
FIG. 6A is a cross-sectional side view of the device of FIG. 1 positioned over the clitoris of the user in use.

Referring also to FIGS. 6 and 6A, the method of application of the device 10 (FIG. 1) to the user's body is described. The user compresses the tip portion 16, thereby deforming the tip portion and reducing the air volume within the entire interior vacuum chamber 18. The device 10 is then comfortably fitted over the clitoris 39 with the body-contacting surface 29 of the flange 26 placed in contact with the anterior vaginal vault tissue surrounding the clitoris 39 and the tip portion 16 is released, permitting the device to expand to its original shape. The restorative deformation of the tip portion causes at least a partial vacuum to be provided within the interior vacuum chamber 18. The vacuum environment serves to produce clitoral engorgement 39' and increased sexual arousal while also serving to maintain the device 10 in reliable sealed engagement with the user. The surrounding labial folds further secure the device 10 to the clitoris 39' and within the anterior vaginal vestibule 33. In this fashion, the labial folds both cover the device 10 and prevent device migration. The user may now discreetly wear the device 10 as she performs her daily tasks without further self-manipulation or embarrassment.

The deformation of the tip portion 16 reduces the air volume within the entire interior vacuum chamber 18 and produces a partial vacuum. The force created by the differential pressure between the outside atmosphere pressure and the pressure within the interior vacuum chamber will attempt to force the intermediate side walls 24 inward toward the center of the vacuum chamber. If the intermediate side walls 24 were deformable (e.g., flat or concave inward), sufficient vacuum applied to the interior vacuum chamber 18 would cause the intermediate side walls 24 to collapse inward toward or into an abutting relationship. In this case, the normally distensible clitoris 39 would be drawn into the compromised interior vacuum chamber 18 and compressed by the abutting intermediate side walls 24. Clitoral tissue could become entrapped and pinched by these abutting side walls. In a preferred embodiment, the outwardly convex shape of the side walls 24 of the present invention acts like an arch, preventing inward movement of the intermediate side walls 24 and thereby preventing clitoral entrapment and/or compression. More precisely, the outwardly convex geometry of the intermediate side walls 24 creates two functional chambers 18*a* and 18*b* which resemble a "bell". The lower vacuum chamber 18*b*, formed by the outwardly convex intermediate side walls, serves as a substantially non-deformable, substantially constant volume vacuum reservoir, while the upper vacuum chamber 18*a*, formed by the tip portion, serves to create the vacuum due to its side wall deformation. In this fashion, the lower vacuum chamber 18*b*evenly distributes suction to the clitoral tissue without compressing, obstructing or pinching clitoral tissue. The height of the device is sufficient to prevent clitoral distension into the upper vacuum chamber 18*a*.

The user can alter the amount of vacuum in the interior vacuum chamber 18 by varying the degree of compression of the tip portion and thus, the amount of air that is displaced. The greater the amount of manual compression to the tip portion, the greater the amount of displaced air and subsequent vacuum. In this manner, the user can advantageously regulate the amount of clitoral suction in order to generate a physiological response, rather than rely upon predetermined vacuum from an external vacuum source. The amount of vacuum necessary to stimulate female sexual arousal may vary depending upon the user and her pre-excitatory a state.

Figure 7:
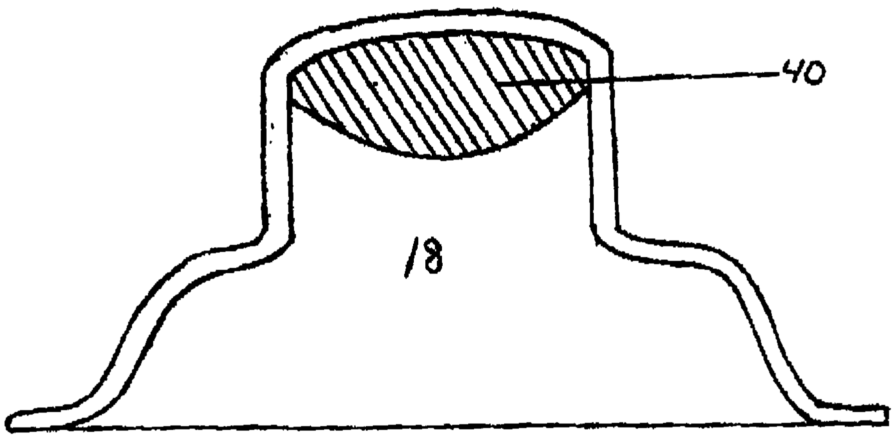
FIG. 7 is a cross-sectional side view an embodiment of the invention having a pharmacologically active material within the device body.
Figure 7A:
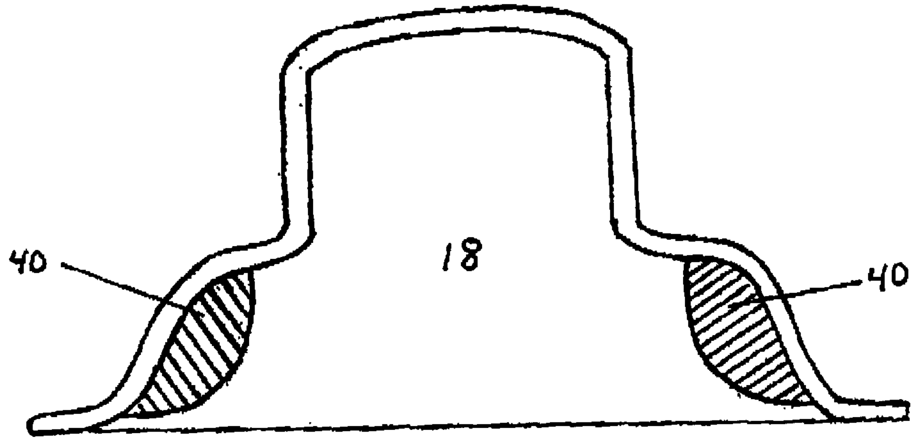
FIG. 7A is a cross-sectional side view of an alternate embodiment of the invention having a pharmacologically active material within the device body.
Figure 7B:
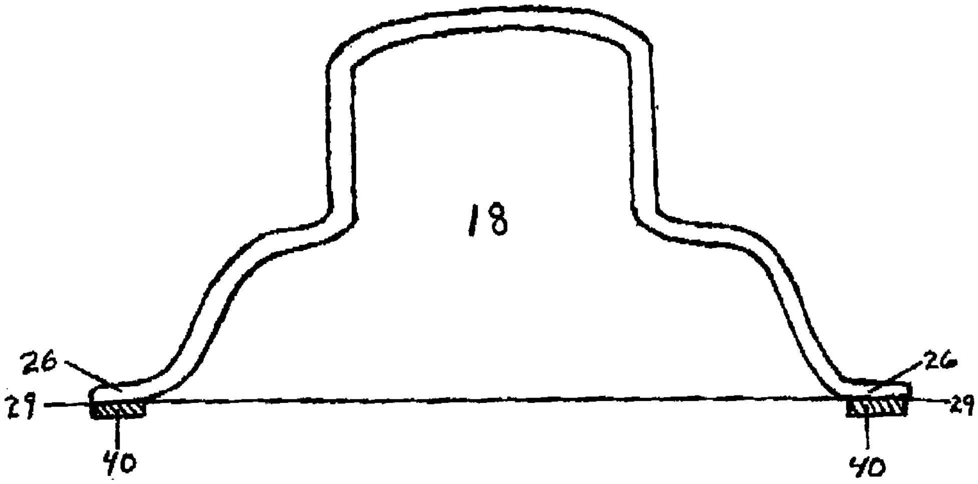
FIG. 7B is a cross-sectional side view of an embodiment of the invention having a pharmacologically active material on the body contacting surface of the flange.
Figure 7C:
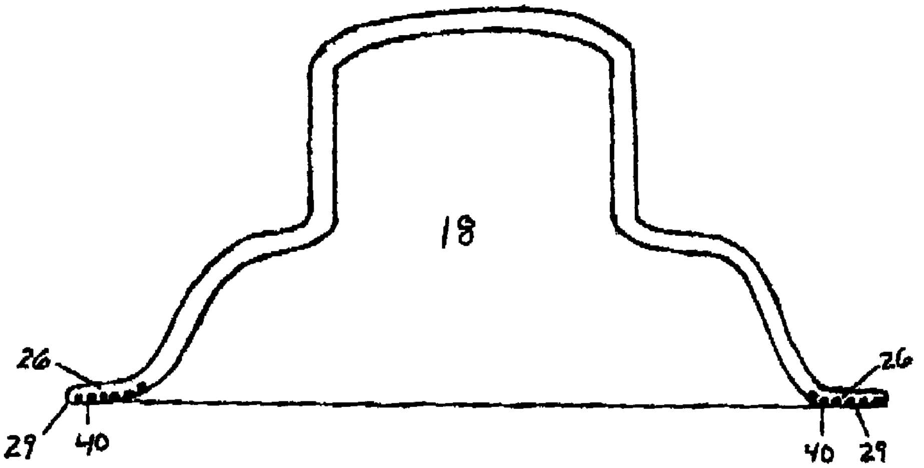
FIG. 7C is a cross-sectional side view of an embodiment of the invention having a pharmacologically active material embedded in a wall of the device.

The efficacy of the device 10 may be enhanced by utilizing it as a delivery system for a variety of pharmacologically active materials that enhance clitoral blood flow, vaginal lubrication, and vaginal sensation. These materials include, but are not limited to: 1.vasoactive agents, both natural and synthetic, that act as vasodilators such as prostaglandins, endothelialderived relaxation factors, vasoactive interstitial polypeptide agonists, smooth muscle relaxants, leukotriene inhibitors, L-arginine, and others; and 2. Medications and substances that increase clitoral stimulation such as estrogen, methyl testosterone, and apomorphine. Such a pharmacologically active material 40 may be provided within the interior vacuum chamber 18, as shown in the embodiments of FIGS. 7 and 7A. When the user compresses the tip portion 16, the agent is pushed downward so as to be in continuous contact with the clitoris. In another embodiment shown in FIG. 7B, a pharmacologically active material 40 is disposed on the body-contacting surface 29 of the flange 26. Upon placement of the device 10 over the clitoris, the user would gently contact the clitoris with the body-contacting surface 29, thereby disposing the agent upon the clitoris. In yet another embodiment shown in FIG. 7C, the pharmacologically active material 40 is embedded in a wall of the device 10 and released upon contact with the vaginal mucosa. The combination of vacuum and continuous exposure to these substances further enhances clitoral blood flow and sexual arousal.

Having described preferred embodiments of the invention, it will now become apparent to one of skill in the art that other embodiments incorporating their concepts may be used. It is felt that these embodiments should not be limited to disclosed embodiments, but rather should be limited only by the spirit and scope of the appended claims. All publications and references cited herein are expressly incorporated herein by reference in their entirety.

What is claimed is:

1. A female stimulation device comprising:

a resilient device body having a tip portion, a flange and an intermediate side wall portion extending outwardly from said tip portion to said flange, wherein said flange is sized and shaped to encompass the female clitoris;

wherein, said tip portion is deformable and defines a vacuum producing upper chamber, and said intermediate side wall portion is outwardly convex comprising a plurality of protuberances and is substantially non-deformable, said intermediate side wall portion defines a vacuum resevoir lower chamber.

2. The device in claim 1 wherein said upper and lower chambers are exposed to one another in use.

3. The device in claim 1 wherein said plurality of protuberances are positioned on an inner surface of the intermediate side wall portion.

4. The device recited in claim 1 further comprising a plurality of protuberances on an outer surface of the intermediate side wall portion.

5. The device in claim 1 wherein the flange portion has a body-contacting surface.

6. The device recited in claim 5 further comprising at least one of: an adhesive, a non-adhesive lubricant, and a hydrophilic, water soluble polymer disposed on the body-contacting surface of the flange.

7. The device recited in claim 1 wherein the tip portion comprises a gripping portion to facilitate application and removal of the device.

8. The device in claim 1 further comprising a pharmacologically active material.

9. The device recited in claim 8 wherein said pharmacologically active material is disposed in said lower chamber.

10. The device recited in claim 8 wherein said pharmacologically active material is disposed on said flange.

11. The device recited in claim 8 wherein said pharmacologically active material is embedded in a wall of the device.

12. The device recited in claim 8 wherein said pharmacologically active material comprises at least one of a vasoactive agent, a medication, or a substance that increases clitoral stimulation.

13. The device recited in claim 1 wherein said device body is of unitary construction.

14. A method for stimulating the clitoris of a female comprising:

providing a resilient device body having a tip portion, a flange and an intermediate side wall portion extending outwardly from said tip portion to said flange, wherein said flange is sized and shaped to encompass the female clitoris, wherein said tip portion is deformable and defines a vacuum producing upper chamber, and said intermediate side wall portion is outwardly convex comprising a plurality of protuberance and is substantially non-deformable, said intermediate side wall portion defines a vacuum reservoir chamber;

compressing said tip portion to reduce air volume within said lower chamber;

placing the device body over the female clitoris so that said flange is placed in contact with tissue surrounding the clitoris;

releasing said tip portion so as to create a vacuum within said lower chamber to produce engorgement of the clitoris.

15. The method of claim 14 further comprising the step of preventing compression of the clitoris.

16. The method of claim 14 further comprising providing a pharmacologically active material within the device body to contact the clitoris.

17. The method of claim 16 wherein said pharmacologically active material comprising a vasoactive agent, a medication, or a substance that increases clitoral stimulation.

18. The method of claim 14 further comprising providing a pharmacologically active material on the flange.

19. The method of claim 18 wherein said pharmacologically active material comprises a vasoactive agent, a medication, or a substance that increases clitorial stimulation.

20. The method of claim 14 further comprising embedding a pharmacologically active material in a wall of the device.

21. The method of claim 20 wherein said pharmacologically active material comprises a vasoactive agent, a medication, or a substance that increases clitoral stimulation.

* * * * *